United States Patent
Pientka et al.

[11] Patent Number: 6,052,196
[45] Date of Patent: Apr. 18, 2000

[54] SENSOR DEVICE FOR DETERMINING THE DEGREE OF WETTING AND/OR SOILING ON WINDOW PANES

[75] Inventors: Rainer Pientka, Achern; Hans Meier, Ottersweier; Francois Schabanel, Saint Maux des Fossés, all of Germany

[73] Assignee: Robert Bosch GmbH, Stuttgart, Germany

[21] Appl. No.: 09/053,574

[22] Filed: Apr. 2, 1998

[30] Foreign Application Priority Data

Apr. 4, 1997 [DE] Germany ............... 197 13 834
Oct. 21, 1997 [DE] Germany ............... 197 46 351

[51] Int. Cl.$^7$ ............... G02B 6/42; G01N 21/55
[52] U.S. Cl. ............... 356/445; 250/227.25
[58] Field of Search ............... 356/445, 388, 356/448, 343, 338; 250/227.25, 239, 574, 341, 339, 349, 227, 577

[56] References Cited

U.S. PATENT DOCUMENTS

| | | | |
|---|---|---|---|
| 4,589,771 | 5/1986 | Watanabe et al. | 356/38 |
| 4,652,745 | 3/1987 | Zanardelli | 250/227 |
| 4,701,613 | 10/1987 | Watanabe et al. | 250/227 |
| 4,798,956 | 1/1989 | Hochstein | 250/341 |
| 5,414,257 | 5/1995 | Stanton | 250/227.25 |
| 5,498,866 | 3/1996 | Bendicks et al. | 250/227.25 |
| 5,917,603 | 6/1999 | Tanaka et al. | 356/388 |

FOREIGN PATENT DOCUMENTS

| | | |
|---|---|---|
| 856564 | 10/1977 | Belgium . |
| 0 299 606 | 1/1989 | European Pat. Off. . |
| 0 371 949 | 6/1990 | European Pat. Off. . |

*Primary Examiner*—Frank G. Font
*Assistant Examiner*—Michael P. Stafira
*Attorney, Agent, or Firm*—Kenyon & Kenyon

[57] ABSTRACT

A sensor device for determining the degree of wetting and/or soiling of a pane in a motor vehicle is provided. The sensor device detects the coating of moisture on the outer side of the pane via an optical beam which is arranged in the area of the pane. The sensor device includes a reflector positioned in the pane, the reflector directing the beam through the pane under conditions of total reflection or reflection at the outer side of the pane and at the reflector. The pane additionally includes a light filter which absorbs a selected wavelength of sunlight. The attenuation is reduced via an optically more absorbent layer of the light filter.

11 Claims, 2 Drawing Sheets

SENSOR DEVICE FOR DETERMINING THE DEGREE OF WETTING AND/OR SOILING ON WINDOW PANES

FIELD OF THE INVENTION

The present invention relates to a sensor device for determining the degree of wetting and/or soiling on window panes.

BACKGROUND INFORMATION

In motor vehicles, to measure the degree of wetting (i.e., moisture) present in the wiper field of windshields or rear windows, a rain sensor is installed on the inner side of the window. If the wiping system is switched on in the automatic operating mode, and the window is wetted with moisture at the location where the sensor is installed, a wiping operation is initiated.

The mode of operation of the sensor is based on an optical principle. In particular, a light beam of known intensity emitted by a transmitter is introduced into the pane at a certain location and is directed through a defined length of the pane by means of repeated total reflection within the pane. At a second selected location, the light beam is directed by means of optical coupling out to a receiver and to a measuring system where the residual light intensity is measured and analyzed.

When the surface of the pane is wetted with drops of water, part of the light beam is no longer completely reflected, but rather emerges from the pane. The resultant loss of intensity of the residual light is a measure of the pane surface wetting. Below a preselected threshold value, a means for cleaning the window pane is then automatically activated.

Rain sensors of this type are often installed in motor vehicles at the level of the rearview mirror to ensure that the driver's vision is not impaired by the sensor housing. In some motor vehicles, however, a light filter, e.g., a green or gray wedge tinting the upper edge of the pane, is situated at this location and is integrated in the windshield. When the wave length of the transmitter beam being used is within a range that is essentially attenuated by the light filter, it is not possible to position the optical rain sensor in the light filter, since the repeated total reflection in the pane causes the light beam to pass through the light filter several times, attenuating it to an unacceptable degree.

SUMMARY OF THE INVENTION

The sensor device of the present invention has the advantage that the transmitter beam of the rain sensor, in passing through the pane, is totally reflected or reflected at a reflecting means in the pane, such that the attenuation resulting from the optically more highly absorbent layer of the light filter is reduced.

Since the conventional windshield of an motor vehicle is comprised of a composite of a plurality of layers, and the light filter is normally designed as an optically more highly absorbent layer of the laminated glass, a reflecting means can be mounted between this layer and the external layer which faces away from the interior of the motor vehicle, so that the transmitter beam is directed through the pane, under conditions of total reflection or reflection at the outer side of the outer layer and at the reflecting means.

Another advantage of the present invention is that the reflecting means can be realized in various ways, so that for laminated glass panes that are variously manufactured or executed, optimal solutions can be found.

Yet another advantage of the present invention is that the optical paths of the light beam in the pane are shorter, the paths being generated by the reflecting means. Thus, assuming a constant length of the measuring distance of the rain sensor, the result is a larger number of reflections, so that an even (homogeneous) illumination of the measuring distance is provided. In this way, the sensitivity of the rain sensor in the area of the measuring distance is evened out (homogenized) and thus increased.

A further advantage of the present invention results from the possibility of eliminating the heating device for heating the inner side of the pane, since the wetting of the inner side of the pane, e.g., through condensation water, exerts practically no additional influence on the moisture-dependent weakening of the signal and thus on the functional reliability of the rain sensor.

DETAILED DESCRIPTION OF THE INVENTION

Figure 1:
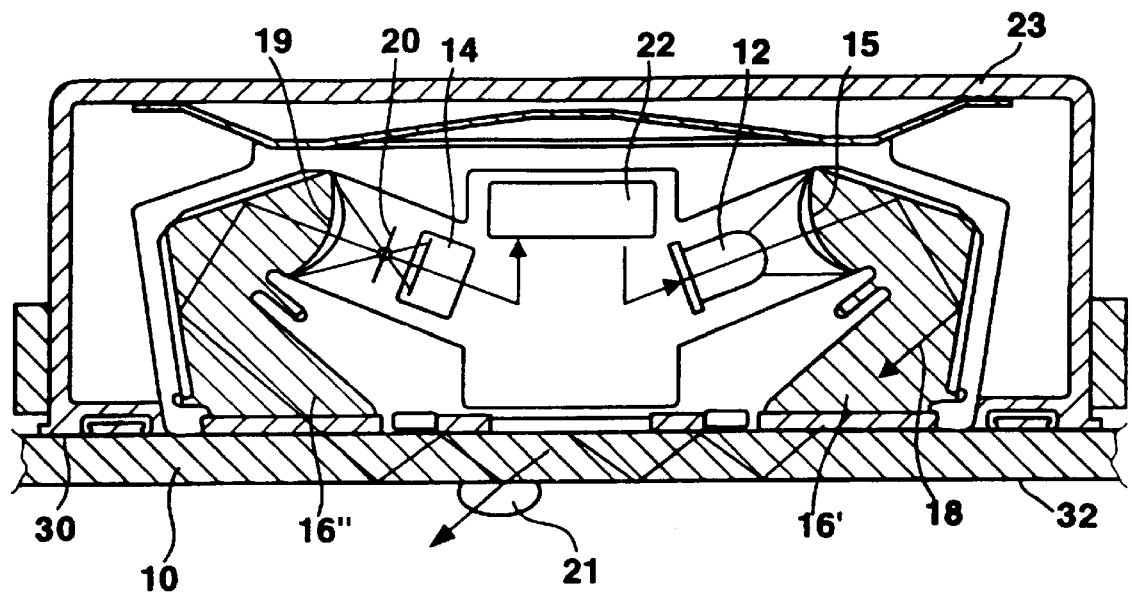
FIG. 1 shows a cross section of a sensor device, comprising an optical rain sensor situated on a conventional pane.

FIG. 1 shows an optical rain sensor mounted on a glass pane 10. Pane 10 may be, for example, a rear window or another pane whose wetting is to be measured. The rain sensor includes as a transmitter 12, e.g., a diode (LED), and a receiver 14, e.g., a photo diode. The transmitter 12, receiver 14, together with two photo conductors 16', 16" and a part of pane 10, constitute an optical measuring circuit. Light emerging from transmitter 12 is focussed at an entry lens 15 of first photo conductor 16' and is deflected towards total-reflecting surfaces, so that, at an output face, it can penetrate into windshield pane 10 at a selected angle as a nearly parallel light beam 18.

With conventional panes 10, after light beam 18 penetrates into pane 10, the beam 18, at outer side 32 and at inner side 30 of pane 10, is totally reflected and/or reflected several times.

At a suitable location, light beam 18 reaches receiver 14, via second photo conductor 16" having a lens-like, curved light-conducting output face 19 and an aperture 20. The quantity of light received by receiver 14 changes as a function of the degree of wetting of pane 10, since, as a result of rain drops 21 situated in the measuring range of the rain sensor, part of light beam 18 passes through pane 10. The signal of receiver 14 is subsequently conducted to an evaluating electronics 22 situated within or outside the rain sensor, where it is processed and evaluated.

The rain sensor and parts of evaluating electronics 22 are arranged in a housing 23. This housing 23, for example, is clipped onto metal clamping connections, which are glued to pane 10.

Figure 2:
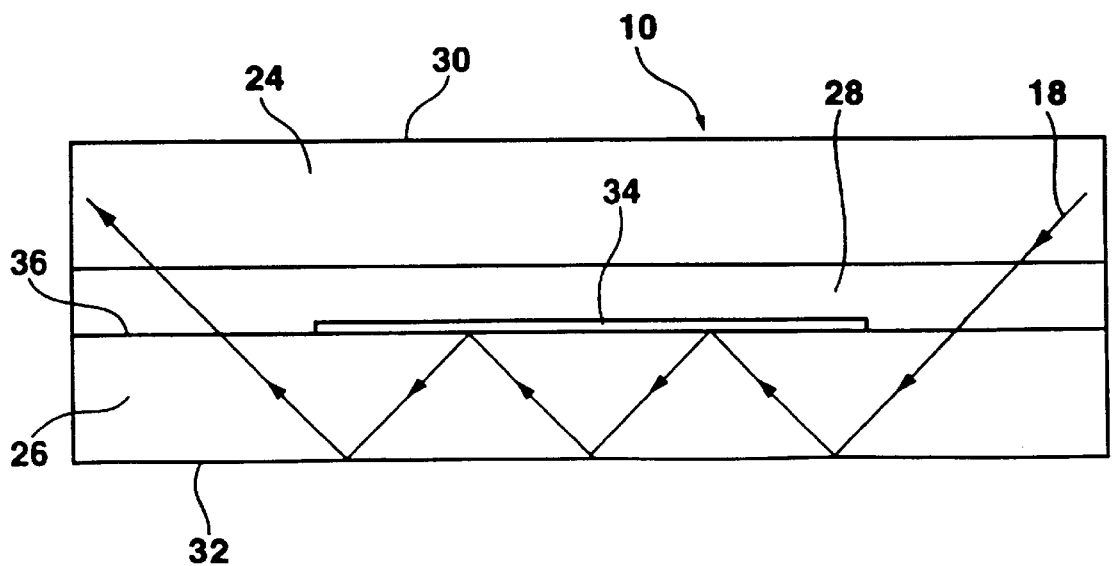
FIG. 2 shows a cross section of a pane in the area of the measuring distance of the rain sensor, according to a first exemplary embodiment of the present invention.

FIG. 2 shows a cross section of a pane 10 in the area of the measuring distance of the rain sensor in accordance with the present invention. Pane 10 is a laminated glass pane having an inner pane 24 facing the motor vehicle interior, an outer pane 26, and, as a light filter, a tinted (or dyed)

laminated glass film 28 arranged between the other layers, which absorbs light of a selected wave length more than inner or outer panes 24, 26. The light filter attenuates the sunlight of a selected wave length range, so that the driver of the motor vehicle is not blinded. In accordance with the invention, a reflecting means 34 is arranged in the area of the measuring distance between inner side 36 of outer pane 26 and film 28, which is more absorbent.

The sensor device of the present invention shown in FIG. 2 functions as follows. In accordance with the present invention, a reflecting means 34 is arranged in the area of the measuring distance of the rain sensor such that the attenuation of light beam 18 by film 28 is reduced, in that light beam 18 traverses film 28 only during the injecting and coupling-out of light beam 18 in or out of pane 10, respectively. Between the injecting and coupling-out of light beam 18, light beam 18, which is evaluated in evaluating electronics 22, is reflected, at the surface of reflecting means 34, back to outer side 32 of pane 10 and does not reach film 28, which is more absorbent.

Reflecting means 34, for example, can be arranged on inner side 36 of outer pane 26 or on the surface of film 28. It is equally possible to insert reflecting means 34 between outer pane 26 and film 28.

For reflecting means 34, for example, a thin metal film, preferably made of aluminum, or a metallically vapor-deposited thin plastic film may be employed. It can be arranged, with adhesive bonding, on inner side 36 of outer pane 32. This reflecting means 34 is nevertheless visible.

A further specific embodiment of reflecting means 34 can be realized by an essentially transparent film or layer (coating), whose refractive index is different from that of pane 10. The difference in refractive index causes, at reflecting means 34, a reflection of part of diagonal light beam 18. If reflecting means 34 is selected optimally, the light transmission of pane 10 will, in this case, be improved for light beam 18 emitted by transmitter 12, and/or the losses that are independent of wetting will be reduced.

Reflecting means 34 can also be realized through directly coating inner side 36 of outer pane 32, e.g., through brushing on, vapor depositing, or adhesion bonding.

Reflecting means 34 is generally adjusted to the light emitted from the transmitter 12 and having a known wave length, such that reflecting means 34 reflects the light of this wave length the most (in comparison with other wave lengths).

Due to the shorter optical paths of light beam 18 in pane 10, given a constant length of the measuring distance, the number of total reflections or reflections increases, resulting in a more even illumination of the measuring distance, i.e., of outer side 32 of pane 10. In this way, the sensitivity of the rain sensor is evened out in the area of the entire measuring distance.

If reflecting means 34 is used, neither condensation water nor any other type of wetting on inner side 30 of inner pane 24, both of which are undesirable with conventional sensor devices, has any further influence on the functional reliability of the rain sensor, since no total reflection takes place on the inner side 30 of pane 10, which would thus cause a possible coupling-out of light beam 18 during wetting. Therefore, condensation water on inner side 30 cannot lead to a weakening of the signal at receiver 14. As a result, there is no need for heating in the rain sensor, intended to prevent condensation on inner side 30 of inner pane 24.

Figure 3:
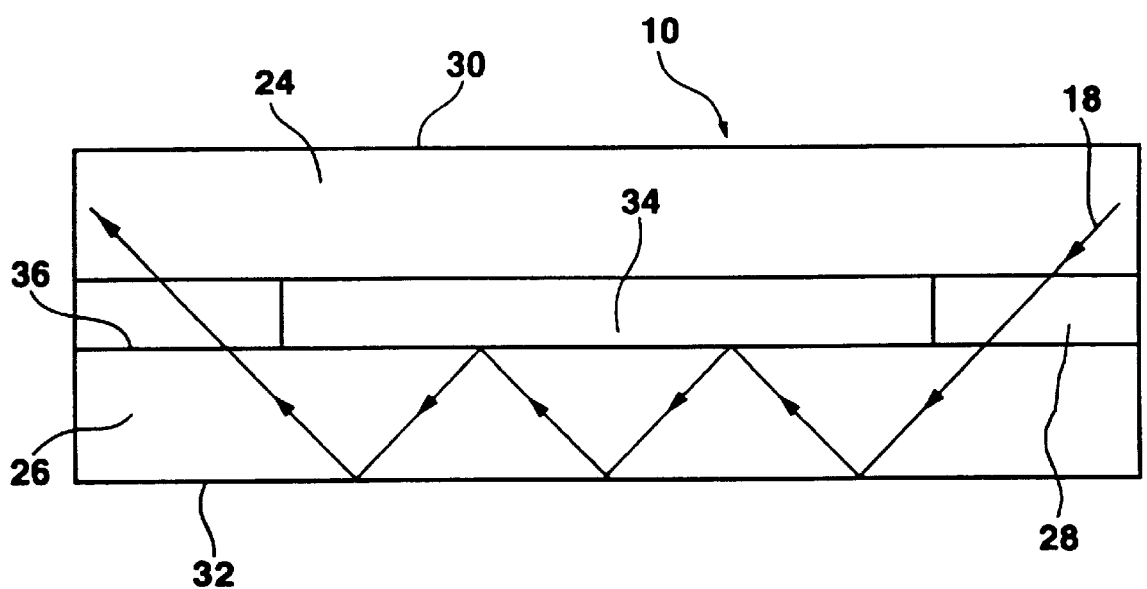
FIG. 3 shows a cross section of an improved pane in the area of the measuring distance of the rain sensor, according to a second exemplary embodiment of the present invention.

FIG. 3 shows a further exemplary embodiment of the sensor device of the present invention in a cross section of pane 10 in the area of the measuring distance of the rain sensor, analogously to FIG. 2. Pane 10 includes a composite of layers, having an inner pane 24, an outer pane 26, and a film 28 inserted between two panes 24, 26, the film 28 being punched out at inner side 36 of outer pane 26, in the area of an inner total reflection of light beam 18.

The punching out takes place during the manufacture of pane 10. In subsequently assembling two panes 24, 26, a hollow space is formed as a reflecting means 34 for light beam 18, the hollow space, depending on the manufacturing process, being filled with humidity-free air at low pressure, or containing a vacuum.

As a result of the relationship of the refractive index of outer pane 26 and the air or vacuum in the hollow space, as well as of the refractive index of the angle of incidence of light beam 18, the latter moves through a total reflection, at inner side 36 of outer pane 26, and at outer side 32 of outer pane 26. In the hollow space, however, no humidity can accumulate which might result in parts of light beam 18 being coupled out from outer pane 26 and passing into the hollow space and inner pane 24. Therefore, the total reflection in pane 10 is independent of humidity.

What is claimed is:

1. A sensor device for detecting moisture on an outer side of a pane in a motor vehicle, comprising:

a reflector positioned between two of a plurality of layers of the pane, a transmitter emitting a beam into the pane, the beam being directed into the pane at the outer side of the pane and at the reflector under a condition of at least one of total reflection and reflection wherein, within a portion of the pane that is coextensive with a length of the reflector, the beam is reflected within the pane in a path bounded by the outer side of the pane and a side of the reflector facing the outer side of the plane; and a receiver detecting the beam emerging from the pane.

2. The sensor device according to claim 1, wherein the plurality of layers include a first layer and an outer pane layer, the first layer including a material that renders the first layer optically more absorbent than the outer pane layer, the reflector being positioned between the first layer and the outer pane layer.

3. The sensor device according to claim 2, wherein the material of the first layer includes a light filter, the light filter including one of a tinted laminate glass film and a poly vinyl butyryl.

4. The sensor device according to claim 2, wherein the reflector is one of i) mounted on an inner side of the outer pane layer, ii) mounted on a surface of the first layer, and iii) inserted between the outer pane layer and the first layer.

5. The sensor device according to claim 1, wherein the reflector includes at least one of a metal film and a metallically vapor-deposited plastic film.

6. The sensor device according to claim 1, wherein the reflector has a refractive index that is different from a refractive index of an adjacent one of the plurality of layers.

7. The sensor device according to claim 1, wherein the reflector is one of i) coated on an adjacent one of the plurality of layers, ii) vapor deposited on the adjacent one of the plurality of layers, and iii) adhesively bonded to the adjacent one of the plurality of layers.

8. The sensor device according to claim 1, wherein the reflector includes a hollow layer, the hollow layer being filled with a gas and having a refractive index that is different than a refractive index of an adjacent one of the plurality of layers.

9. The sensor device according to claim 1, wherein the reflector includes a hollow layer having a vacuum and having a refractive index that is different than a refractive index of an adjacent one of the plurality of layers.

10. The sensor device according to claim 1, wherein the beam is reflected within the portion of the pane that is coextensive with the length of the reflector a number of times that is greater than a number of times the beam is reflected in another portion of the pane that is outside the portion of the plane that is coextensive with the length of the reflector.

11. The sensor device according to claim 2, wherein the beam does not impinge on the first layer while the beam travels through the portion of the plane that is coextensive with the length of the reflector.

* * * * *